(12) United States Patent
Jing

(10) Patent No.: US 11,083,514 B2
(45) Date of Patent: Aug. 10, 2021

(54) MOXIBUSTION JAR AND MEDICINAL MOXIBUSTION DEVICE

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventor: Yangkun Jing, Beijing (CN)

(73) Assignees: BOE TECHNOLOGY GROUP CO., LTD., Beijing (CN); HEFEI BOE OPTOELECTRONICS TECHNOLOGY LTD., Hefei (CN)

( * ) Notice: Subject to any disclaimer, the term of this patent is extended or adjusted under 35 U.S.C. 154(b) by 822 days.

(21) Appl. No.: 15/751,417

(22) PCT Filed: Jul. 27, 2017

(86) PCT No.: PCT/CN2017/094705
§ 371 (c)(1),
(2) Date: Feb. 8, 2018

(87) PCT Pub. No.: WO2018/049929
PCT Pub. Date: Mar. 22, 2018

(65) Prior Publication Data
US 2020/0222280 A1 Jul. 16, 2020

(30) Foreign Application Priority Data
Sep. 19, 2016 (CN) .......................... 201610832832.9

(51) Int. Cl.
*A61B 18/06* (2006.01)
*A61M 37/00* (2006.01)

(52) U.S. Cl.
CPC ........ *A61B 18/06* (2013.01); *A61B 2018/064* (2013.01); *A61M 37/00* (2013.01); *A61M 2037/0007* (2013.01)

(58) Field of Classification Search
CPC .............. A61B 18/06; A61B 2018/064; A61B 2018/00291; A61M 37/00;
(Continued)

(56) References Cited

U.S. PATENT DOCUMENTS

| 3,946,733 | A | * | 3/1976 | Han | ....................... | A61M 35/30 |
| | | | | | | 604/24 |
| 8,353,882 | B1 | * | 1/2013 | Pelkus | ................. | A61N 5/0624 |
| | | | | | | 604/290 |
| 2010/0286750 | A1 | | 11/2010 | Nakamura | | |

FOREIGN PATENT DOCUMENTS

| CN | 2291921 Y | 9/1998 |
| CN | 101411666 A | 4/2009 |

(Continued)

OTHER PUBLICATIONS

First Office Action issued in Chinese Application No. 201610832832.9 dated Apr. 17, 2018 (with English translation).
(Continued)

*Primary Examiner* — Bradley J Osinski
(74) *Attorney, Agent, or Firm* — McDermott Will and Emery LLP

(57) ABSTRACT

A moxibustion jar and a medicinal moxibustion device are provided. The moxibustion jar comprises a jar body (10), with a first opening (11) being formed on the bottom of the jar body (10); and, an adsorption chamber (20) which is arranged on the jar body (10). The adsorption chamber (20) is configured to absorb the jar body (10) onto an object to be cauterized, and the jar body (10) is configured to generate medicine vapor and allow the medicine vapor to reach the first opening (11) to come into contact with the object to be
(Continued)

cauterized. In this moxibustion jar, by providing the adsorption chamber (20) on the jar body (10), the moxibustion jar can be absorbed onto the surface of the skin of a human body. On this basis, a medicine liquid evaporation device (30) evaporates a liquid medicine to form medicine vapor, so that the gas pressure inside the jar body (10) is increased and the absorption rate of the skin is thus improved. Moreover, the moxibustion jar and the medicinal moxibustion device are simple and clean, and have few operation limitations and better therapeutic effects.

17 Claims, 7 Drawing Sheets

(58) Field of Classification Search
CPC ..... A61M 2037/0007; A61H 2039/005; A61H 39/00; A61H 2201/0292; A61H 39/06
See application file for complete search history.

(56) References Cited

FOREIGN PATENT DOCUMENTS

| | | |
|---|---|---|
| CN | 101653626 A | 2/2010 |
| CN | 101925340 A | 12/2010 |
| CN | 202005913 U | 10/2011 |
| CN | 202724237 U | 2/2013 |
| CN | 203252894 U | 10/2013 |
| CN | 103622812 A | 3/2014 |
| CN | 204468649 U | 7/2015 |
| CN | 205198431 U | 5/2016 |
| CN | 106420335 A | 2/2017 |
| CN | 206334109 U | 7/2017 |
| JP | 2007-181720 A | 7/2007 |
| WO | 2007/021093 A1 | 2/2007 |
| WO | 2007/126209 A1 | 11/2007 |

OTHER PUBLICATIONS

International Search Report issued in International Patent Application No. PCT/CN2017/094705, dated Nov. 3, 2017; with English translation.

Written Opinion of the International Searching Authority issued in International Patent Application No. PCT/CN2017/094705, dated Nov. 3, 2017; with English translation.

* cited by examiner

MOXIBUSTION JAR AND MEDICINAL MOXIBUSTION DEVICE

CROSS-REFERENCE TO RELATED APPLICATION

The present application is a national phase entry under USC 371 of International Patent Application No. PCT/CN2017/094705 filed on 27 Jul. 2017, which claims priority to Chinese Patent Application No. 201610832832.9 filed on Sep. 19, 2016, titled "MOXIBUSTION JAR AND MEDICINAL MOXIBUSTION DEVICE", the disclosure of which is hereby incorporated by reference in its entirety.

TECHNICAL FIELD

Embodiments of the present disclosure relate to a moxibustion jar and a medicinal moxibustion device.

BACKGROUND OF THE INVENTION

The moxibustion therapy is a therapeutic method of stimulating a specific part of a human body for purpose of preventing and treating diseases.

The moxa-moxibustion therapy, as an example of the conventional moxa-moxibustion therapy, is a method in which moxa down is prepared by making use of wormwood leaves as raw material and then rolled to form cylindrical moxa sticks and the moxa sticks are burnt at a certain acupuncture point in various ways to directly or indirectly cause proper warm stimulation so as to achieve the purpose of disease treatment and health-caring through the conduction of meridians and collaterals.

SUMMARY

The embodiments of the present disclosure provide a moxibustion jar and a medicinal moxibustion device, which can improve the absorption rate of medicine liquid during the medicinal moxibustion.

At least one embodiment of the present disclosure provides a moxibustion jar, including: a jar body, with a first opening being formed on the bottom of the jar body; and, an adsorption chamber which is arranged on the jar body. The adsorption chamber is configured to absorb the jar body onto an object to be cauterized. The jar body is configured to generate medicine vapor and allow the medicine vapor to reach the first opening to come into contact with the object to be cauterized.

For example, in the moxibustion jar provided in one embodiment of the present disclosure, the adsorption chamber is arranged around the jar body.

For example, in the moxibustion jar provided in one embodiment of the present disclosure, the adsorption chamber is arranged at the bottom of the jar body.

For example, the moxibustion jar provided in one embodiment of the present disclosure further includes: a vacuum suction tube provided on an outer side of the jar body, with one end of the vacuum suction tube being connected to the adsorption chamber.

For example, in the moxibustion jar provided in one embodiment of the present disclosure, a medicine liquid evaporation device is provided within the jar body and configured to evaporate a liquid medicine into the medicine vapor.

For example, in the moxibustion jar provided in one embodiment of the present disclosure, the medicine liquid evaporation device includes a medicine liquid evaporation chamber having a gas outlet and a microwave generator. The microwave is provided above the medicine liquid evaporation chamber and configured to evaporate the liquid medicine in the medicine liquid evaporation chamber into gas and discharge the gas from the gas outlet.

For example, in the moxibustion jar provided in one embodiment of the present disclosure, a second opening is formed on the top of the jar body The moxibustion jar further includes a piston provided at the second opening. A sealing ring is provided between the piston and an inner wall of the jar body and used for adjusting the pressure of gas within the jar body.

For example, in the moxibustion jar provided in one embodiment of the present disclosure, the microwave generator is fixed to the piston.

For example, in the moxibustion jar provided in one embodiment of the present disclosure, the other end of the vacuum suction tube is located within the jar body and close to the piston.

For example, in the moxibustion jar provided in one embodiment of the present disclosure, the medicine liquid evaporation chamber includes a bottom wall and a side wall. The bottom wall is close to the first opening on the bottom of the jar body. The bottom wall is a gas filter screen which comes into contact with and is fixed to the inner wall of the jar body. The gas filter screen is used for allowing gas to pass therethrough. There is a gap between the side wall of the medicine liquid evaporation chamber and the inner wall of the jar body.

For example, in the moxibustion jar provided in one embodiment of the present disclosure, the medicine liquid evaporation chamber is in an upturned funnel shape.

For example, in the moxibustion jar provided in one embodiment of the present disclosure, an infrared heating device is further provided within the jar body, and arranged below the medicine liquid evaporation device. The infrared heating device is arranged around the inner wall of the jar body.

For example, the moxibustion jar provided in one embodiment of the present disclosure further includes, on the bottom of the jar body, a first flexible adsorption layer which is located on an inner layer of the adsorption chamber; and, a second flexible adsorption layer which is located on an outer layer of the adsorption chamber. A temperature detection device is further provided within the jar body and is arranged in the first flexible adsorption layer. The temperature detection device includes a probe which extends into the first opening on the bottom of the jar body.

For example, in the moxibustion jar provided in one embodiment of the present disclosure, a gas pressure detection device is further provided within the jar body. The moxibustion jar further includes a pressure control valve arranged on the jar body to release the pressure inside the jar body when the gas pressure detected by the gas pressure detection device is greater than a preset threshold.

At least one embodiment of the present disclosure further provides a medicinal moxibustion device, including the moxibustion jar described above.

For example, the medicinal moxibustion device provided in one embodiment of the present disclosure further includes a control device which is connected to the microwave generator in the moxibustion jar and configured for controlling the intensity of a microwave signal transmitted by the microwave generator.

For example, in the medicinal moxibustion device provided in one embodiment of the present disclosure, the control device includes an AC power supplier and a rectification control circuit. The rectification control circuit is connected to the AC power supplier and the microwave generator. The rectification control circuit is configured for processing an AC signal provided by the AC power supplier to supply power to the microwave generator so as to control the intensity of the microwave signal transmitted by the microwave generator.

For example, in the medicinal moxibustion device provided in one embodiment of the present disclosure, the control device further includes a controller connected to the rectification control circuit. The controller is connected to the temperature detection device and configured to control the rectification control circuit according to the temperature detected by the temperature detection device so as to control the intensity of the microwave signal transmitted by the microwave generator.

For example, in the medicinal moxibustion device provided in one embodiment of the present disclosure, the control device further includes a controller connected to the rectification control circuit. The controller is connected to both the gas pressure detection device and the pressure control valve, and configured to control the pressure control valve to release the pressure inside the jar body when the gas pressure detected by the gas pressure detection device is greater than a preset threshold and to control the rectification control circuit according to the gas pressure detected by the gas pressure detection device so as to control the intensity of the microwave signal transmitted by the microwave generator.

For example, the medicinal moxibustion device provided in one embodiment of the present disclosure further includes a medicine liquid storage tank which is connected to the medicine liquid evaporation chamber in the moxibustion jar through a hose. A control valve is provided on the hose. The control device is further connected to the control valve and configured to control the flow rate of medicine liquid flowing from the medicine liquid storage tank to the medicine liquid evaporation chamber.

For the moxibustion jar and the medicinal moxibustion device provided by the present disclosure, by providing the adsorption chamber on the jar body, the moxibustion jar can be absorbed onto the surface of the skin of a human body. On this basis, the medicine vapor generated in the jar body increases the gas pressure inside the jar body, thus improving the absorption rate of the skin. Moreover, the moxibustion jar and the medicinal moxibustion device are simple and clean, and have few operation limitations and better therapeutic effects. When the medicine vapor flows to a specified acupuncture point along with the blood, the tissue metabolism will be enhanced, the phagocytosis of white blood cells will be enhanced, and the absorption and elimination of pathological products will be facilitated.

BRIEF DESCRIPTION OF THE DRAWINGS

To describe the technical solutions in the embodiments of the present disclosure or in the prior art more clearly, the drawings to be used in the descriptions of the embodiments or the prior art will be briefly described below. Apparently, the drawings described hereinafter are some of embodiments of the present invention, and a person of ordinary skill in the art can obtain other drawings according to these drawings without paying any creative effort.

DETAILED DESCRIPTION

The technical solutions of the present disclosure will be clearly and completely described below with reference to the drawings of the present disclosure. Apparently, the embodiments described herein are merely a part but not all of the embodiments of the present invention. All other embodiments obtained by a person of ordinary skill in the art without paying any creative effort on the basis of the embodiments in the present invention shall fall into the protection scope of the present invention.

From the studies, the inventor of the present application found that the conventional moxa-moxibustion therapy had low absorption rate, and disease treatment and heath-caring effects are limited.

Therefore, the embodiments of the present disclosure provide a moxibustion jar and a medicinal moxibustion device. The moxibustion jar includes: a jar body, with a first opening being formed on the bottom of the jar body; and, an adsorption chamber which is arranged on the jar body. The adsorption chamber is configured to absorb the jar body onto an object to be cauterized. The jar body is configured to generate medicine vapor and allow the medicine vapor to reach the first opening to come into contact with the object to be cauterized. Thus, by providing the adsorption chamber on the jar body, the moxibustion jar can be absorbed onto the surface of the skin of a human body. On this basis, a medicine evaporation device evaporates liquid medicine into the medicine vapor, so that the gas pressure inside the jar body is increased and the absorption rate of the skin is thus improved. Moreover, the moxibustion jar and the medicinal moxibustion device are simple and clean, and have few operation limitations and better therapeutic effects. When the medicine vapor flows to a specified acupuncture point along with the blood, the tissue metabolism will be enhanced, the phagocytosis of white blood cells will be enhanced, and the absorption and elimination of pathological products will be promoted.

Figure 1:
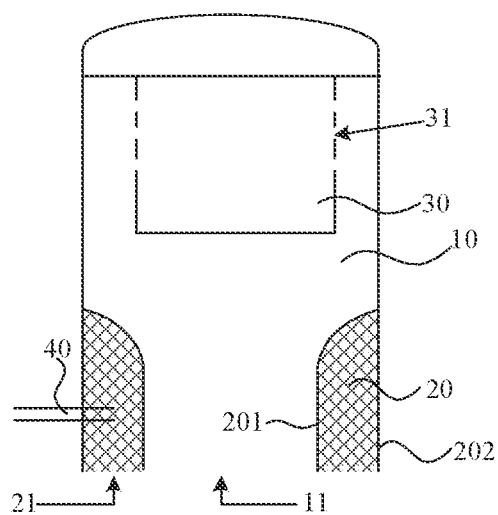
FIG. 1 is a first internal structure diagram of a moxibustion jar according to the present disclosure.
Figure 2:
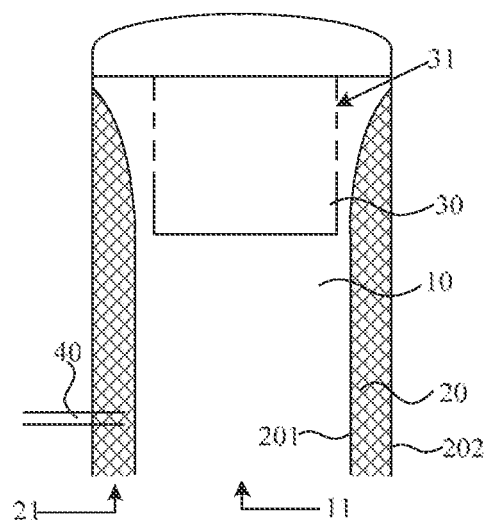
FIG. 2 is a second internal structure diagram of the moxibustion jar according to the present disclosure.

An embodiment of the present disclosure provides a moxibustion jar, as shown in FIGS. 1 and 2, including a jar body 10, with a first opening 11 being formed on the bottom of the jar body 10. The moxibustion jar further includes an adsorption chamber 20 arranged on the jar body 10. The adsorption chamber 20 is used for absorbing the jar body 10 onto an object to be cauterized, for example, onto the skin of a human body. The jar body 10 is used for generating medicine vapor and allowing the medicine vapor to reach the first opening 11 to come into contact with the object to be cauterized.

In the moxibustion jar provided in this embodiment, by providing the adsorption chamber on the jar body, the moxibustion jar can be absorbed onto the surface of the skin of a human body. On this basis, the medicine vapor generated in the jar body increases the gas pressure inside the jar body, thus improving the absorption rate of the skin. Moreover, the moxibustion jar and the medicinal moxibustion device are simple and clean, and have few operation limitations and better therapeutic effects. When the medicine vapor flows to a specified acupuncture point along with the blood, the tissue metabolism will be enhanced, the phagocytosis of white blood cells will be enhanced, and the absorption and elimination of pathological products will be promoted.

For example, in some examples, as shown in FIGS. 1 and 2, the moxibustion jar further includes a vacuum suction tube 40 provided on an outer side of the jar body 10. One end of the vacuum suction tube 40 is connected to the adsorption chamber 20. Thus, by the vacuum suction tube, the pressure of the adsorption chamber can be reduced or even the adsorption chamber can be vacuumed, so that the adsorption onto the object to be cauterized is realized. Of course, the present disclosure includes this method but is not limited thereto, and other ways of reducing pressure of the adsorption chamber or even vacuuming the adsorption chamber are also possible.

For example, in an example, as shown in FIGS. 1 and 2, a medicine liquid evaporation device 30 is further provided within the jar body 10 and configured to evaporate a liquid medicine into medicine vapor. The medicine vapor evaporated from the medicine liquid evaporation device 30 reaches the first opening 11 on the bottom of the jar body 10.

For example, the jar body 10 and the adsorption chamber 20 are formed integrally.

It is to be noted that, in the present disclosure, the material of the jar body 10 will not be limited as long as the material is not toxic and can realize the heat insulation function. In the present disclosure, the shape of the jar body 10 will not be limited either, and the shape and size of the jar body 10 matched with a part of the human body can be manufactured. In addition, the adsorption chamber 20 has an adsorption port 21 which is located in the same plane as the first opening 11 on the bottom of the jar body 10.

Figure 3:
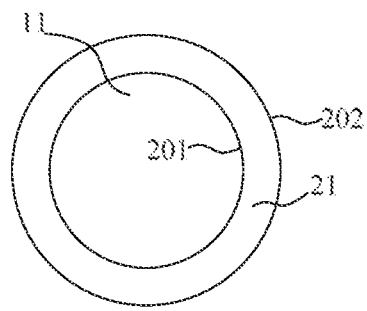
FIG. 3 is a first bottom view of the moxibustion jar according to the present disclosure.

For example, as shown in FIG. 3, when in use, the moxibustion jar is absorbed onto the surface of the skin of the human body by the adsorption port 21 of the adsorption chamber 20.

For example, in some examples, as shown in FIG. 1, the adsorption chamber 20 can be arranged only at the bottom of the jar body 10, or, as shown in FIG. 2, the adsorption chamber 20 can extend from the bottom of the jar body 10 to the top of the jar body 10.

For example, in some examples, a through hole may be formed on the adsorption chamber 20 to realize the connection of the vacuum suction tube 40 to the adsorption chamber 20.

For example, in some examples, for the connection of the vacuum suction tube 40 to the adsorption chamber 20, one end of the vacuum suction tube 40 may be inserted into the adsorption chamber 20, or the vacuum suction tube 40 may be embedded into the jar body 10 without extending into the adsorption chamber 20.

For example, in some examples, to ensure the airtightness of the jar body 10, the through hole on the jar body 10 can be sealed by a sealing ring.

For example, in some examples, the structure and fixation way of the medicine liquid evaporation device 30 will not be limited as long as the medicine liquid evaporation device 30 can evaporate the liquid medicine into the medicine vapor and can allow the medicine vapor to reach the first opening 11 on the bottom of the jar body so as to act on the skin of the human body.

For example, in some examples, the medicine vapor can be evaporated into the jar body 10 through a gas outlet 31 formed on the medicine liquid evaporation device 30, and then passes through the first opening 11 on the bottom of the jar body to act on the skin of the human body. In addition, the liquid medicine in the medicine liquid evaporation device 30 will not be limited. For example, the liquid medicine may be extract liquid of wormwood, or may be extract liquid of other Chinese herbal medicines.

For the moxibustion jar provided embodiments of the present disclosure, by providing the adsorption chamber 20 on the jar body 10 and providing the vacuum suction tube 40 connected to the adsorption chamber 20, the moxibustion jar can be absorbed onto the surface of the skin of a human body. On this basis, the medicine vapor generated in the jar body 10 increases the gas pressure inside the jar body, thus improving the absorption rate of the skin. Moreover, the moxibustion jar is simple and clean, and has few operation limitations and better therapeutic effects. When the medicine vapor flows to a specified acupuncture point along with the blood, the tissue metabolism will be enhanced, the phagocytosis of white blood cells will be enhanced, and the absorption and elimination of pathological products will be promoted.

For example, in some examples, due to the low cost, nontoxicity and high temperature resistance of the ceramic material, the jar body 10 in the present disclosure is preferably made of ceramic material.

For example, in some examples, as shown in FIG. 1, the adsorption chamber 20 is arranged at the bottom of the jar body 10.

For example, in some examples, the adsorption chamber 20 consists of an inner layer 201 and an outer layer 202. When the adsorption chamber 20 is arranged on an outer side of the jar body 10, the inner layer 201 of the adsorption chamber 20 may be the wall of the jar body 10. When the adsorption chamber 20 is arranged on an inner side of the jar body 10, the outer layer 202 of the adsorption chamber 20 may be the wall of the jar body 10.

For example, in some examples, by arranging the adsorption chamber 20 at the bottom of the jar body 10, the space within the jar body 10 can be saved, so that there is a larger space within the jar body 10 to be filled with the medicine vapor.

Figure 4:
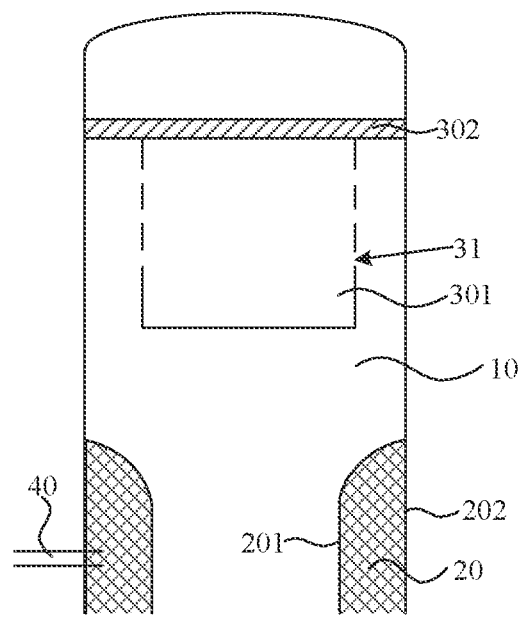
FIG. 4 is a third internal structure diagram of the moxibustion jar according to the present disclosure.

For example, in some examples, as shown in FIG. 4, the medicine liquid evaporation device 30 includes a medicine liquid evaporation chamber 301 and a microwave generator 302. The microwave generator 302 is arranged above the medicine liquid evaporation chamber 301. The medicine liquid evaporation chamber 301 has a gas outlet 31. The liquid medicine in the medicine liquid evaporation chamber 301 is evaporated into gas under the action of the microwave generator 302, and the gas is discharged from the gas outlet 31.

For example, in some examples, the microwave generator 302 can generate a plurality of microwaves which radiate downward at different positions, to ensure that the radiation of microwave signals transmitted by the microwave generator 302 is balanced as a whole.

For example, in some examples, the arranging position and the number of the gas outlet(s) 31 will not be limited as long as the medicine vapor discharged from the gas outlet 31 can enter the jar body 19 and reach the first opening 11 on the bottom of the jar body so as to act on the skin of the human body.

For example, in some examples, the moxibustion jar should further include a power transmission line for supplying power to the microwave generator 302. On this basis, the power transmission line may extend to the outside of the jar body 10 through the through hole formed on the jar body 10.

The microwave generator 302 is utilized in the present disclosure. The energy of a microwave signal transmitted by the microwave generator 302 can evaporate the liquid medicine in the medicine liquid evaporation chamber into medicine vapor, and can warm and stimulate the local skin so as to result in hyperemia and angiotelectasis, so that the absorption rate of the medicine vapor is further improved.

Figure 5:
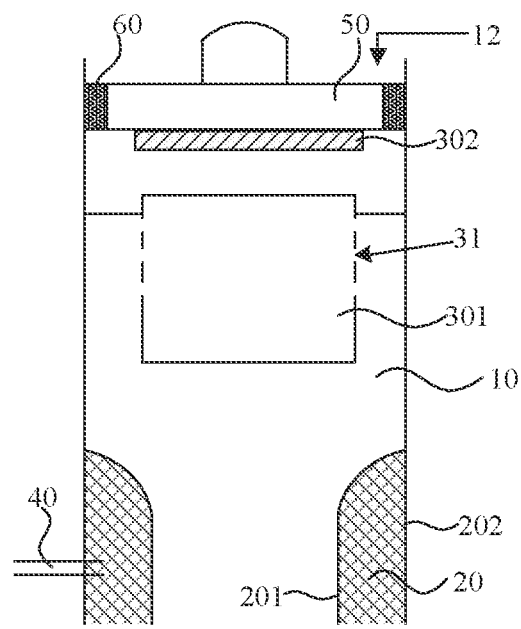
FIG. 5 is a fourth internal structure diagram of the moxibustion jar according to the present disclosure.

For example, in some examples, as shown in FIG. 5, a second opening 12 is formed on the top of the jar body 10. The moxibustion jar further includes a piston 50 provided at the second opening 12 on the top of the jar body 10. A sealing ring 60 is provided between the piston 50 and an inner wall of the jar body 10. The piston 50 is used for adjusting the pressure of gas within the jar body 10.

For example, in some examples, the piston 50 can be moved up and down manually. In this case, preferably, a bump is further provided on the piston 50 so that it is convenient to push or pull the piston. Of course, the piston 50 can also be moved up and down automatically. In this case, a piston control structure connected to the piston 50 is further required and included, to control the up-and-down movement of the piston 50.

It is to be noted that the top of the jar body 10 is described with respect to the bottom of the jar body 10. For the jar body 10 itself, the top of the jar body 10 is still airtight actually with the piston 50 being arranged at the second opening on the top of the jar body.

In the present disclosure, with the arrangement of the piston 50, the gas pressure inside the jar body 10 can be increased when the piston 50 is pushed down, so that the absorption rate of the medicine vapor by the human body is further improved.

For example, in some examples, as shown in FIG. 5, in the case where the medicine liquid evaporation device 30 includes a medicine liquid evaporation chamber 301 and a microwave generator 302, the microwave generator 302 is fixed to the piston 50.

Thus, it is convenient for fixing the microwave generator 302, and the microwave generator 302 can be located above the medicine liquid evaporation chamber 301, so that the evaporation efficiency of the medicine liquid is improved.

Figure 6:
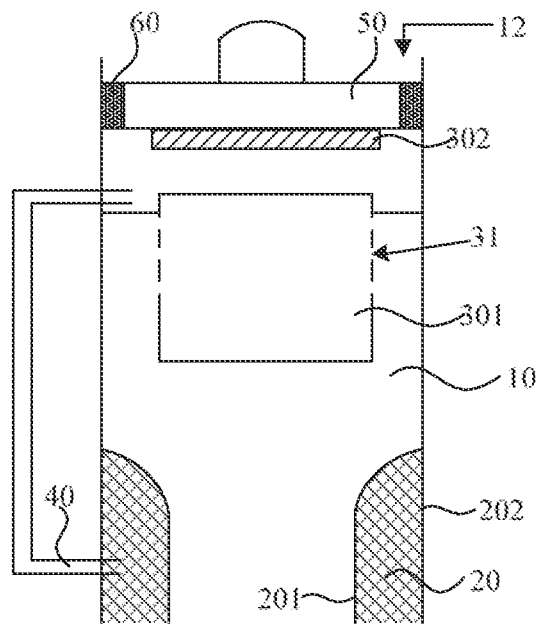
FIG. 6 is a fifth internal structure diagram of the moxibustion jar according to the present disclosure.

For example, in some examples, as shown in FIG. 6, the other end of the vacuum suction tube 40 is located within the jar body 10 and close to the piston 50.

Here, by pulling the piston 50 up, air within the adsorption chamber 20 can be pumped out by the vacuum suction tube 40, so that the moxibustion jar is absorbed onto the surface of the skin of the human body. On this basis, a valve may be provided on a side of the vacuum suction tube 40 close to the adsorption chamber 20. After the moxibustion jar is absorbed onto the surface of the skin of the human body, the valve is controlled to be closed, and the gas inside the vacuum suction tube 40 is thus not circulated. Thus, when it is required to increase the gas pressure inside the jar body 10, the moxibustion jar will not be separated from the skin even if the piston 50 is pushed down.

Of course, it is also possible to push down the piston 50 to discharge air within the adsorption chamber 20 so as to absorb the moxibustion jar onto the surface of the skin of the human body. In this case, no valve is required.

In the present disclosure, by providing the other end of the vacuum suction tube 40 within the jar body 10 and close to the piston 50, the moxibustion jar can be absorbed onto the surface of the skin of the human body by moving the piston 50, so that the structure of the moxibustion jar becomes simpler.

Figure 7:
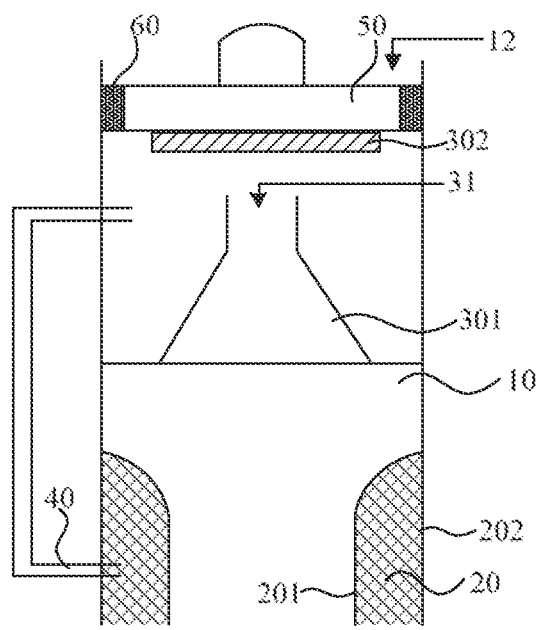
FIG. 7 is a sixth internal structure diagram of the moxibustion jar according to the present disclosure.

For example, in some examples, as shown in FIG. 7, the medicine liquid evaporation chamber 301 includes a bottom wall and a side wall. The bottom wall is arranged close to the first opening 11 on the bottom of the jar body 10. The bottom wall is a gas filter screen which comes onto contact with and is fixed to the inner wall of the jar body 10. The gas filter screen is used for allowing gas to pass therethrough. There is a gap between the side wall of the medicine liquid evaporation chamber 301 and the inner wall of the jar body 10. The medicine liquid evaporation chamber 301 is in an upturned funnel shape.

Here, the gas filter screen allows gas to pass therethrough and does not allow liquid to flow therethrough. The gas filter screen may be made of polyester fiber material, for example, polytetrafluoroethylene.

In the present disclosure, by using the gas filter screen which comes into contact with and is fixed to the inner wall of the jar body 10, the medicine liquid evaporation chamber 301 can be fixed, and the medicine vapor discharged from the gas outlet 31 of the medicine liquid evaporation chamber 301 is allowed to pass through a portion of the gas filter screen which is within the gap between the side wall of the medicine liquid evaporation chamber 301 and the inner wall of the jar body 10 so as to act on the skin of the human body. Although part of the medicine vapor will be condensed during the movement of the medicine vapor from the medicine liquid evaporation chamber 301 to the gas outlet 31, the medicine liquid evaporation chamber 31 in the present disclosure is in an upturned funnel shape, so the condensed medicine vapor can flow back to the medicine liquid evaporation chamber 301, so that the utilization of the medicine liquid is improved.

Figure 8:
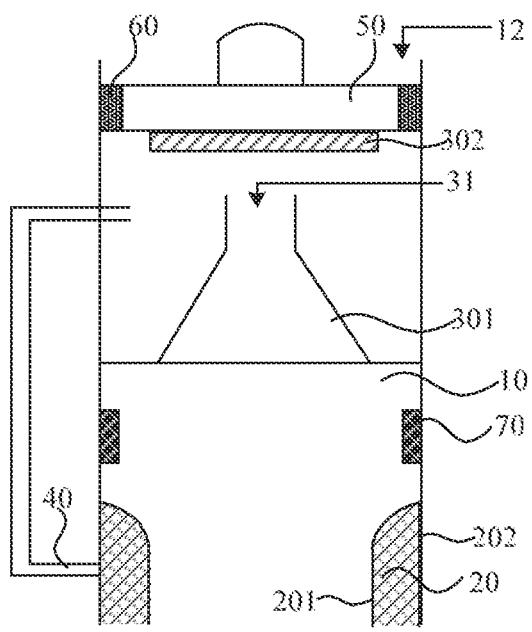
FIG. 8 is a seventh internal structure diagram of the moxibustion jar according to the present disclosure.

For example, in some examples, as shown in FIG. 8, an infrared heating device 70 is further provided within the jar body 10 and arranged below the medicine liquid evaporation device 30. The infrared heating device 70 is arranged around the inner wall of the jar body 10.

For example, in some examples, the infrared heating device 70 may be fixed on the inner wall of the jar body 10. Of course, the infrared heating device may also be fixed within the jay body 10 in other ways, and this will not be limited herein.

For example, in some examples, the infrared heating device 70 may be an infrared heating tube. On this basis, the infrared heating tube is preferably arranged in a spiral manner.

In the present disclosure, with the arrangement of the infrared heating device 70, the skin and the medicine vapor can be additionally heated, and the absorption rate of the medicine vapor by the human body is further improved. In addition, the infrared light emitted by the infrared heating device 70 has the effects of accelerating blood circulation, increasing metabolism, relieving pains, improving muscular relaxation, generating massage effect, improving microcirculation (promoting circulation and removing stasis), enhancing immunity, increasing the cell viability and enzyme activity, facilitating the conditioning mechanism of the human body itself, mediating physiological functions and the like. By arranging the infrared heating device 70 around the inner wall of the jar body 10, the skin and the medicine vapor can be irradiated uniformly.

Figure 9:
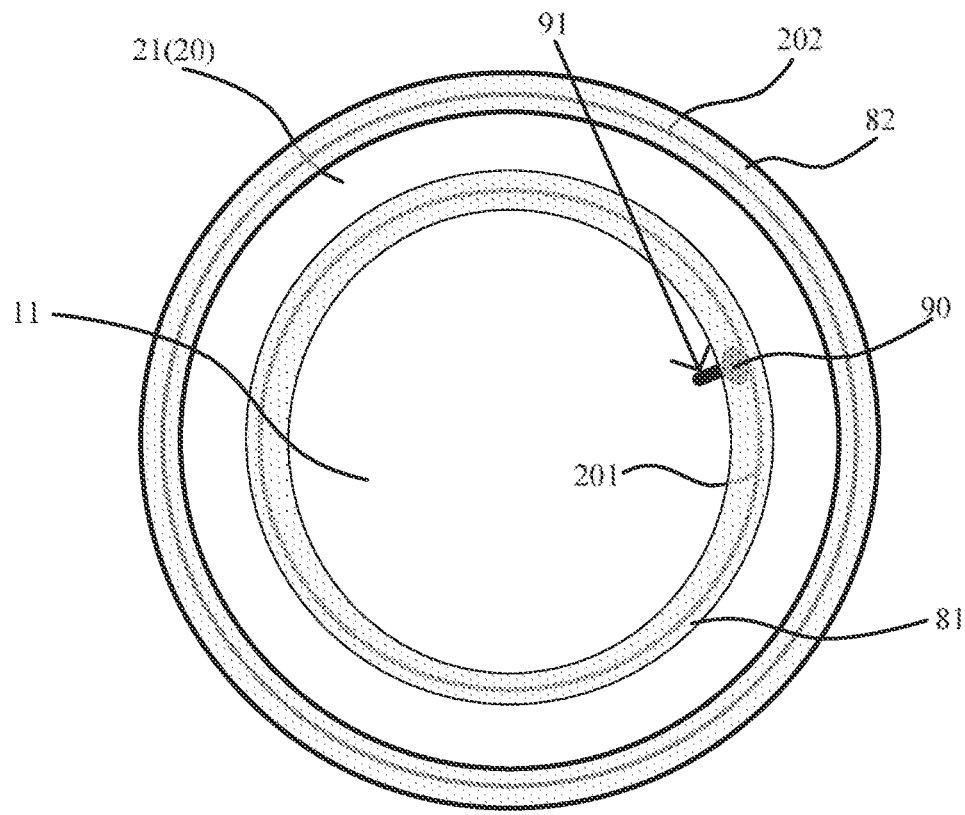
FIG. 9 is a second bottom view of the moxibustion jar according to the present disclosure.

For example, in some examples, as shown in FIG. 9, the moxibustion jar further includes, on the bottom of the jar body 10, a flexible adsorption layer SI which is located on the inner layer 201 of the adsorption chamber 20, and a second flexible adsorption layer 82 which is located on the outer layer 202 of the adsorption chamber 20.

For example, in some examples, a temperature detection device 90 is further provided within the jar body 10 and arranged in the first flexible adsorption layer 81. The temperature detection device 90 includes a probe 91 which extends into the first opening 11 on the bottom of the jar body.

It is to be noted that, the flexible adsorption layers are made of flexible material as long as the airtightness between the adsorption chamber 20 and the skin of the human body can be improved. The temperature detection device 90 may be a temperature sensor. When the moxibustion jar is absorbed onto the surface of the skin of the human body through the adsorption chamber 20, the probe 91 of the temperature detection device 90 extending out from the first flexible adsorption layer 81 comes into contact with the skin of the human body at the first opening 11 on the bottom of the jar body.

In the present disclosure, on one hand, with the arrangement of the first flexible adsorption layer 81 and the second flexible adsorption layer 82, the airtightness between the adsorption chamber 20 and the skin of the human body can be improved, and the adsorption effect is thus better. On the other hand, the energy of the microwave signal transmitted by the microwave generator 302 can be controlled by the temperature detected by the temperature detection device 90, and the temperature of the medicine vapor can be thus controlled to prevent from scalding the skin, so that the activity of the medicine can be improved and better penetration effect is realized.

For example, in some examples, the first flexible adsorption layer 81 is made of conductive rubber material. Of course, the second flexible adsorption layer 82 may be made of conductive rubber material or other flexible adsorption material too.

For example, in some examples, the conductive rubber material is preferably pressure-sensitive conductive rubber material. The adsorption pressure between the flexible adsorption layers and the skin can be detected through the pressure-sensitive conductive rubber material, so that the adsorption chamber 20 is ensured to be firmly absorbed onto the skin.

For example, in some examples, for example, the conductive rubber material may be carbon nanotube rubber.

In the present disclosure, by allowing the first flexible adsorption layer 81 to be made of conductive rubber material, the temperature signal detected by the temperature detection device 90 can be output, and it is convenient for wiring.

Figure 10:
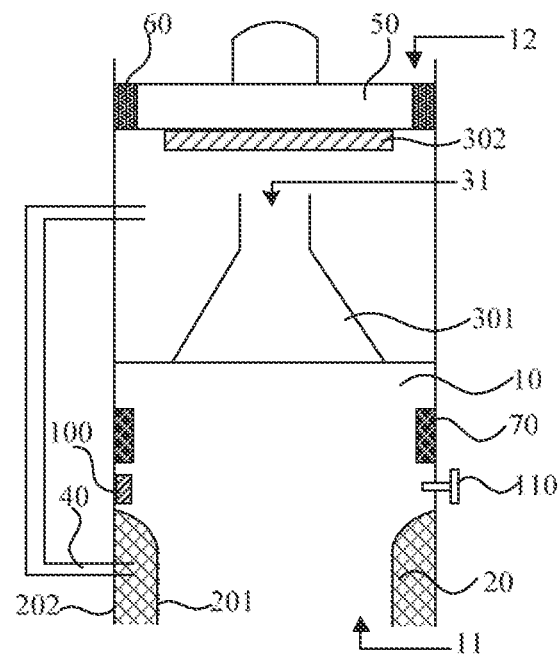
FIG. 10 is an eighth internal structure diagram of the moxibustion jar according to the present disclosure.

For example, in some examples, as shown in FIG. 10, a gas pressure detection device 100 is further provided within the jar body 10. On this basis, the moxibustion jar further includes a pressure control valve 110 arranged on the jar body 10 to release the pressure inside the jar body 10 when the gas pressure detected by the gas pressure detection device 100 is greater than a preset threshold.

For example, in some examples, the gas pressure detection device 100 may be a gas pressure sensor. The pressure control valve 110 is fixed on the wall of the jar body 10, and extends into the jar body 10 through a through hole on the jar body 10. On this basis, the through hole on the jar body 10 can be sealed by a sealing ring.

Since the pressure-sensitive conductive rubber material can realize pressure detection, in the present disclosure, the gas pressure detection device 100 is preferably a pressure-sensitive conductive rubber film which is arranged around the inner wall of the jar body 10.

In the present disclosure, the gas pressure inside the jar body 10 is detected by the gas pressure detection device 100, and the gas pressure inside the jar body 10 is controlled within a certain range by the pressure control valve 110, so that the safety of the jar body 10 can be improved.

An embodiment of the present disclosure further provides a medicinal moxibustion device, including the moxibustion jar described above.

For the medicinal moxibustion device provided by the present disclosure, by providing the adsorption chamber 20 around the jar body 10 and providing the vacuum suction tube 40 connected to the adsorption chamber 20, the moxibustion jar can be absorbed onto the surface of the skin of a human body. On this basis, since the medicine liquid evaporation device 30 evaporates a liquid medicine to form medicine vapor, the gas pressure inside the jar body is increased and the absorption rate of the skin is thus improved. Moreover, the medicinal moxibustion device is simple and clean, and has few operation limitations and better therapeutic effects. When the medicine vapor flows to a specified acupuncture point along with the blood, the tissue metabolism will be enhanced, the phagocytosis of white blood cells will be enhanced, and the absorption and elimination of pathological products will be promoted.

Figure 11:
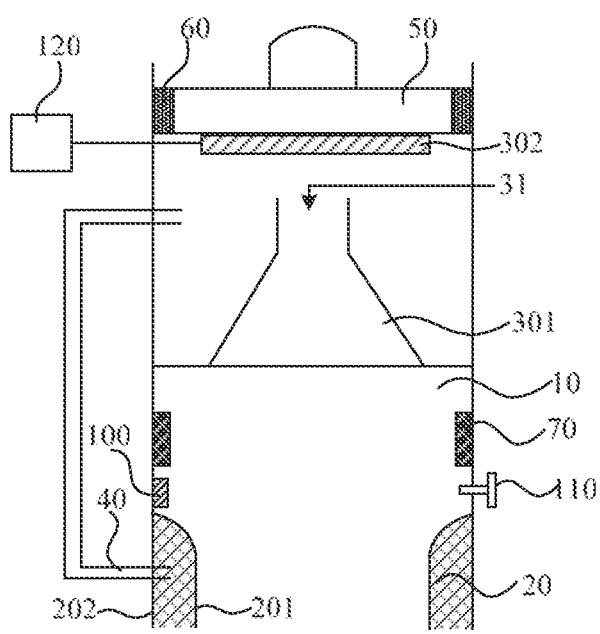
FIG. 11 is a ninth internal structure diagram of the moxibustion jar according to the present disclosure.

For example, in some examples, as shown in FIG. 11, the medicinal moxibustion device further includes a control device 120. The control device 120 is connected to the microwave generator 302 in the moxibustion jar and used for controlling the intensity of a microwave signal transmitted by the microwave generator 302.

Under the circumstance that the medicine liquid evaporation device 30 includes a medicine liquid evaporation chamber 301 and a microwave generator 302, the control device 120 can control the intensity of the microwave signal transmitted by the microwave generator 302, and thus controlling the speed of evaporation of the liquid medicine in the medicine liquid evaporation chamber 301. Furthermore, the energy of the microwave signal can warm and stimulate the local skin so as to result in hyperemia and angiotelectasis, so that the absorption of the medicine vapor can be facilitated.

Figure 12:
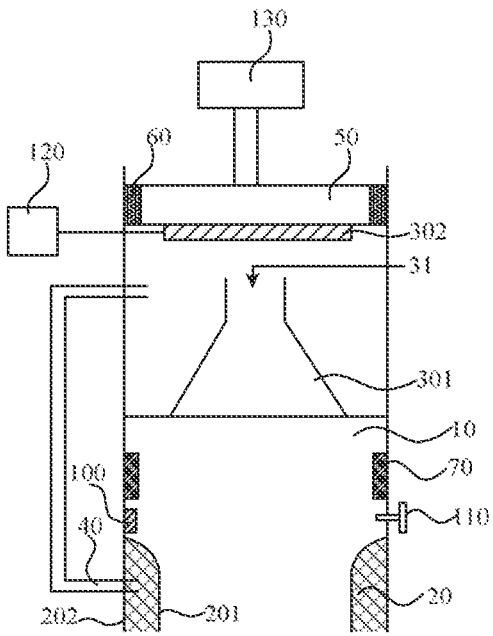
FIG. 12 is a tenth internal structure diagram of the moxibustion jar according to the present disclosure.

For example, in some examples, as shown in FIG. 12, the medicinal moxibustion device further includes a piston control structure 130 which is connected to the piston 50 and used for controlling the up-and-down movement of the piston 50.

For example, in some examples, the piston control structure 130 can be a combination of one or more functional components or elements, which can drive the piston 50 to move up and down.

In the medicinal moxibustion device provided in this embodiment, by controlling the movement of the piston 50 by the piston control structure 130, the operation is simpler and more convenient.

Figure 13:
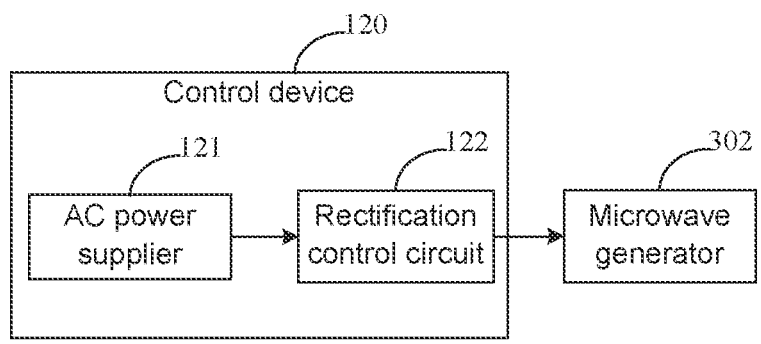
FIG. 13 is a first schematic diagram of units included in a control device and a connection relationship between these units and a microwave generator according to the present disclosure.

For example, in some examples, as shown in FIG. 13, the control device 120 includes an AC power supply device 121 and a rectification control circuit 122. The rectification control circuit 122 is connected to both the AC power supplier 121 and the microwave generator 302. The rectification control circuit 122 is used for processing an AC signal provided by the AC power supplier 121 to supply power to the microwave generator 302 so as to control the intensity of the microwave signal transmitted by the microwave generator 302.

In the medicinal moxibustion device provided in this embodiment, AC current from the mains supply is converted into DC current suitable for the microwave generator 302 through the rectification control circuit 122, which controls the intensity of the microwave signal transmitted by the microwave generator 302.

Figure 14:
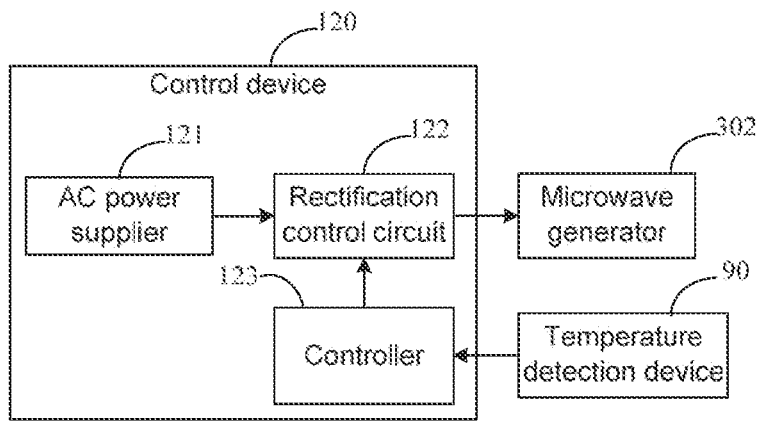
FIG. 14 is a second schematic diagram of units included in a control device and a connection relationship between these units and the microwave generator according to the present disclosure.

For example, in some examples, as shown in FIG. 14, the control device 120 further includes a controller 123 connected to the rectification control circuit 122. The controller 123 is connected to the temperature detection device 90 to control the rectification control circuit 122 according to the temperature detected by the temperature detection device 90 so as to control the intensity of the microwave signal transmitted by the microwave generator 302.

Of course, if the moxibustion jar further includes an infrared heating device 70. During controlling the intensity of the microwave signal transmitted by the microwave generator 302, the controller 123 can also control the heating temperature of the infrared heating device 70 according to the temperature detected by the temperature detection device 90.

By receiving the temperature detected by the temperature detection device 90, the controller 123 control the rectification control circuit 122, thus controlling the intensity of the microwave signal transmitted by the microwave generator 302, and further controlling the energy of the microwave signal transmitted by the microwave generator 302. Accordingly, the temperature of the medicine vapor can be controlled to prevent from scalding the skin, the activity of the medicine can be improved, and better penetration effect can be realized.

Figure 15:
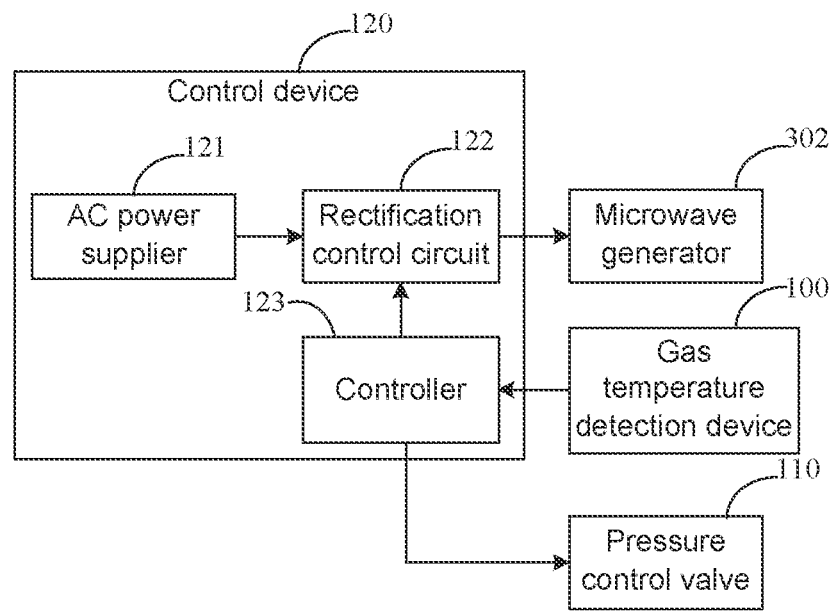
FIG. 15 is a third schematic diagram of units included in a control device and a connection relationship between these units and the microwave generator according to the present disclosure.

For example, in some examples, as shown in FIG. 15, the control device 120 further includes a controller 123 connected to the rectification control circuit 122. The controller 123 is connected to both the gas pressure detection device 100 and the pressure control valve 110. The controller 123 is configured to control the pressure control valve 110 to release the pressure inside the jar body 10 when the gas pressure detected by the gas pressure detection device 100 is greater than a preset threshold and to control the rectification control circuit 122 according to the gas pressure detected by the gas pressure detection device 100 so as to control the intensity of the microwave signal transmitted by the microwave generator 302.

By receiving the gas pressure inside the jar body 10 detected by the gas pressure detection device 100, the controller 123 controls the rectification control circuit 122, thus controlling the intensity of the microwave signal transmitted by the microwave generator 302, so that the energy of the microwave signal transmitted by the microwave generator 302 is controlled. Moreover, by controlling the pressure control valve 110 by the controller 123, the gas pressure inside the jar body 10 is controlled within a certain range, and the safety of the jar body is thus ensured.

Figure 16:
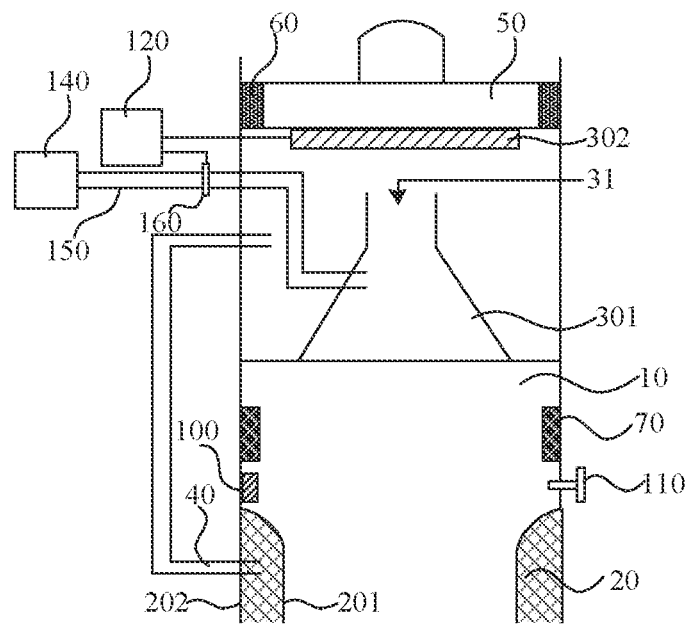
FIG. 16 is an eleventh internal structure diagram of the moxibustion jar according to the present disclosure.

Based on the above description, in some examples, as shown in FIG. 16, the medicinal moxibustion device further includes a medicine liquid storage tank 140 which is connected to the medicine liquid evaporation chamber 301 in the moxibustion jar through a hose 150. A control valve 160 is provided on the hose 150. The control device 120 is further connected to the control valve 160 to control the flow rate of medicine liquid in the medicine liquid storage tank 140 into the medicine liquid evaporation chamber 301.

For example, in some examples, the hose 150 may be a liquid transfer hose. The control valve 160 is an electric control valve.

In the medicinal moxibustion device provided in this embodiment, on one hand, the medicine liquid storage tank 140 can continuously supply medicine liquid to the medicine liquid evaporation chamber 301; and on the other hand, the control valve 160 can be controlled by the control device 120 according to the intensity of the microwave signal transmitted by the microwave generator 302, so as to control the flow rate of medicine liquid into the medicine liquid evaporation chamber 301.

For example, in some examples, the controller is executed by a microprocessor which executes one or more operations and/or functions as described above. For example, in some examples, the controller as a whole or partially is proceed by specifically configured hardwares (for example, one or more application-specific integrated circuits).

The foregoing descriptions merely show specific implementations of the present invention, and the protection scope of the present invention is not limited thereto. Any person of skill in the art can readily conceive of variations or replacements within the technical scope disclosed by the embodiments of the present invention, and these variations or replacements shall fall into the protection scope of the present invention. Accordingly, the protection scope of the present invention shall be subject to the protection scope of the claims.

What is claimed is:
1. A moxibustion jar, comprising:
a jar body, with a first opening being formed on the bottom of the jar body; and
an adsorption chamber which is arranged on the jar body, wherein the adsorption chamber is configured to attach the jar body onto an object to be cauterized, and the jar body is configured to generate medicine vapor and allow the medicine vapor to reach the first opening to come into contact with the object to be cauterized; and
a medicine liquid evaporation device is provided within the jar body and configured to evaporate a liquid medicine to form the medicine vapor; the medicine liquid evaporation device includes:
a medicine liquid evaporation chamber having a gas outlet; and a microwave generator, which is provided above the medicine liquid evaporation chamber and configured to evaporate the liquid medicine in the medicine liquid evaporation chamber into gas and discharge the gas from the gas outlet.

2. The moxibustion jar according to claim 1, wherein the adsorption chamber is arranged around the jar body.

3. The moxibustion jar according to claim 1, wherein the adsorption chamber is arranged at the bottom of the jar body.

4. The moxibustion jar according to claim 1; further comprising: a vacuum suction tube provided on an outer side of the jar body, with one end of the vacuum suction tube being connected to the adsorption chamber.

5. The moxibustion jar according to claim 1, wherein a second opening is formed on the top of the jar body; the moxibustion jar further comprises a piston provided at the second opening; a sealing ring is provided between the piston and an inner wall of the jar body and used for adjusting the pressure of gas within the jar body.

6. The moxibustion jar according to 5, wherein the microwave generator is fixed to the piston.

7. The moxibustion jar according to claim 5, wherein the other end of the vacuum suction tube is located within the jar body and close to the piston.

8. The moxibustion jar according to claim 1, wherein the medicine liquid evaporation chamber comprises a bottom wall and a side wall; the bottom wall is close to the first opening on the bottom of the jar body; the bottom wall is a gas filter screen which comes into contact with and is fixed to the inner wall of the jar body; the gas filter screen is used for allowing gas to pass therethrough; and, there is a gap between the side wall of the medicine liquid evaporation chamber and the inner wall of the jar body.

9. The moxibustion jar according to claim 1, wherein the medicine liquid evaporation chamber is in an upturned funnel shape.

10. The moxibustion jar according to claim 1, wherein an infrared heating device is further provided within the jar body and arranged below the medicine liquid evaporation device; and, the infrared heating device is arranged around the inner wall of the jar body.

11. The moxibustion jar according to claim 1, further comprising: on the bottom of the jar body;
a first flexible adsorption layer which is located on an inner layer of the adsorption chamber; and
a second flexible adsorption layer which is located on an outer layer of the adsorption chamber;
wherein a temperature detection device is further provided within the jar body and arranged in the first flexible adsorption layer; and, the temperature detection device comprises a probe which extends into the first opening on the bottom of the jar body.

12. The moxibustion jar according to claim 1, wherein a gas pressure detection device is further provided within the jar body; the moxibustion jar further comprises a pressure control valve arranged on the jar body to release the pressure inside the jar body when the gas pressure detected by the gas pressure detection device is greater than a preset threshold.

13. A medicinal moxibustion device, comprising the moxibustion jar according to claim 1, wherein the medicinal moxibustion device further comprises a control device which is connected to the microwave generator in the moxibustion jar and configured for controlling the intensity of a microwave signal transmitted by the microwave generator.

14. The medicinal moxibustion device according to claim 13, wherein the control device comprises an AC power supplier and a rectification control circuit; and
the rectification control circuit is connected to the AC power supplier and the microwave generator, and the rectification control circuit is configured for processing an AC signal provided by the AC power supplier to supply power to the microwave generator so as to control the intensity of the microwave signal transmitted by the microwave generator.

15. The medicinal moxibustion device according to claim 14, a temperature detection device is provided within a jar body of the moxibustion jar wherein the control device further comprises a controller connected to the rectification control circuit, and the controller is connected to the temperature detection device anc configured to control the rectification control circuit according to the temperature detected by the temperature detection device so as to control the intensity of the microwave signal transmitted by the microwave generator.

16. The medicinal moxibustion device according to claim 14, a gas pressure detection device is provided within a jar body of the moxibustion jar, wherein the control device further comprises a controller connected to the rectification control circuit; and, the controller is connected to both the gas pressure detection device and the pressure control valve, and configured to control the pressure control valve to release the pressure inside the jar body when the gas pressure detected by the gas pressure detection device is greater than a preset threshold and to control the rectification control circuit according to the gas pressure detected by the gas pressure detection device so as to control the intensity of the microwave signal transmitted by the microwave generator.

17. The medicinal moxibustion device according to claim 13, further comprising a medicine liquid storage tank which is connected to the medicine liquid evaporation chamber in the moxibustion jar through a hose; and
a control valve is provided on the hose, and the control device is further connected to the control valve and configured to control the flow rate of medicine liquid flowing from the medicine liquid storage tank to the medicine liquid evaporation chamber.

* * * * *